United States Patent
Kerl et al.

(10) Patent No.: US 10,456,352 B2
(45) Date of Patent: Oct. 29, 2019

(54) OXIDATION DYEING AGENT WITH SPECIAL HYDROXY-TERMINATED, AMINE-FUNCTIONALIZED SILICONE POLYMERS

(71) Applicant: Henkel AG & Co. KGaA, Duesseldorf (DE)

(72) Inventors: Sylvia Kerl, Hamburg (DE); Susanne Hagenow, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/751,168

(22) PCT Filed: Jul. 5, 2016

(86) PCT No.: PCT/EP2016/065808
§ 371 (c)(1),
(2) Date: Feb. 8, 2018

(87) PCT Pub. No.: WO2017/029015
PCT Pub. Date: Feb. 23, 2017

(65) Prior Publication Data
US 2018/0228719 A1 Aug. 16, 2018

(30) Foreign Application Priority Data

Aug. 18, 2015 (DE) .................. 10 2015 215 714

(51) Int. Cl.
| | | |
|---|---|---|
| *A61Q 5/10* | (2006.01) | |
| *A61K 8/898* | (2006.01) | |
| *A61Q 5/06* | (2006.01) | |
| *A61K 8/41* | (2006.01) | |
| *A61K 8/49* | (2006.01) | |

(52) U.S. Cl.
CPC .............. *A61K 8/898* (2013.01); *A61K 8/415* (2013.01); *A61K 8/494* (2013.01); *A61Q 5/065* (2013.01); *A61Q 5/10* (2013.01); *A61K 2800/4324* (2013.01); *A61K 2800/88* (2013.01); *A61K 2800/882* (2013.01)

(58) Field of Classification Search
CPC .......... A61Q 5/10; A61K 8/415; A61K 8/494; A61K 8/347; A61K 8/42; A61K 2800/88; A61K 2800/4324; A61K 2800/882; A61K 8/898

See application file for complete search history.

(56) References Cited

U.S. PATENT DOCUMENTS

| 8,821,592 B1* | 9/2014 | Gross | A61K 8/416 8/405 |
|---|---|---|---|
| 2003/0152534 A1* | 8/2003 | Legrand | A61K 8/35 424/61 |
| 2010/0125956 A1* | 5/2010 | Koike | A61K 8/23 8/429 |
| 2012/0305416 A1* | 12/2012 | Miyabe | A45D 34/00 206/223 |

FOREIGN PATENT DOCUMENTS

| DE | 102013226358 A1 | 6/2015 | |
|---|---|---|---|
| EP | 1464321 A1 | 10/2004 | |
| FR | 2895242 A1 | 6/2007 | |
| WO | WO2013/013861 A2 * | 1/2013 | A61Q 5/10 |

OTHER PUBLICATIONS

STIC Search Report dated Mar. 14, 2019.*
EPO, International Search Report and Written Opinion issued in International Application No. PCT/EP2016/065808 , dated Sep. 21, 2016.

* cited by examiner

*Primary Examiner* — Eisa B Elhilo
(74) *Attorney, Agent, or Firm* — Lorenz & Kopf, LLP

(57) ABSTRACT

The present disclosure relates to a cosmetic agent for dyeing keratinous fibers, more particularly human hair, containing at least one special hydroxy-terminated, amine-functionalized silicone polymer and at least one oxidative dye precursor and/or one partially-oxidative dye, the use of the at least one hydroxy-terminated, amine-functionalized silicone polymer leading to improved nourishment of the keratinous fibers with extremely low color shift at the same time. The present disclosure also relates to a corresponding kit-of-parts, as well as a method for dyeing keratinous fibers. Finally, the present disclosure relates to the use of the cosmetic agent as contemplated herein, as well as the kit-of-parts as contemplated herein.

18 Claims, No Drawings

OXIDATION DYEING AGENT WITH SPECIAL HYDROXY-TERMINATED, AMINE-FUNCTIONALIZED SILICONE POLYMERS

This application is a U.S. National-Stage entry under 35 U.S.C. § 371 based on International Application No. PCT/EP2016/065808, filed Jul. 5, 2016 which was published under PCT Article 21(2) and which claims priority to German Application No. 10 2015 215 714.8, filed Aug. 18, 2015, which are all hereby incorporated in their entirety by reference.

TECHNICAL FIELD

The present disclosure relates to cosmetic agents for coloring keratin fibers, said agents containing special hydroxy-terminated, amine-functionalized silicone polymers. The present disclosure also relates to a kit-of-parts containing a cosmetic agent as contemplated herein and an oxidant preparation.

The present disclosure also relates to a method for dyeing keratinous fibers using a cosmetic agent as contemplated herein and an oxidant preparation.

Finally, the present disclosure relates to the use of a cosmetic agent as contemplated herein or a kit-of-parts as contemplated herein for increasing the nourishment of keratinous fibers, while minimizing color shift at the same time.

BACKGROUND

Nowadays, human hair is treated with hair care cosmetic preparations in various ways. Including, for example, cleansing the hair with shampoos, nourishing and regenerating with conditioners and masks, as well as bleaching, dyeing and changing the shape of hair with dyes, toning agents, perming agents and styling preparations. Agents for changing or tinting the color of the hair plays a role in such methods. Apart from blonding agents, which decompose natural hair dyes to achieve an oxidative lightening, oxidative hair dyeing is useful to changing the color of hair.

To achieve permanent, intense colors with corresponding fastness properties, so-called oxidative dyes are used. Said dyes may contain oxidative dye precursors, also referred to as developer components and coupler components. The developer components join together or couple with one or more coupler components to form, under the influence of oxidants or atmospheric oxygen, the actual colorants per se. To achieve natural-looking colors, a mix from a large number of oxidative dye precursors (referred to below as OFV) may be used; in many cases, substantive dyes (referred to below as DZ) are still used for tinting.

Oxidative dyes for stabilization of dye precursors during storage and to accelerate reaction during the oxidative use may have an alkaline pH value that is adjusted with alkalizing agents, such as alkanolamines, ammonia or inorganic bases.

The aforementioned oxidation dye precursors (OFV) and alkalizing agents are often incorporated into a cosmetically suitable carrier, such as a cream or a gel. The carrier aides homogeneous distribution and an adequate dwell time of the oxidative dye on the hair.

Commercial oxidative dyes are often formulated in product series including a standardized carrier, which can be combined with the tint-specific OFV combination and alkalizing agents largely without limitation.

Consumers can refer to the hair coloration achievable by employing a hair dye from information on the hair dye packaging and/or from a color chart enclosed with the packaging. For the consumer, it is desirable that the result of the coloration is as close as possible to the color indicated by the manufacturer.

Therefore, hair dyes are tested for the achievable color and also for a multiplicity of application properties ahead of the market launch. However, such tests consider the interactions between OFV and also, where applicable, between DZ and the standardized carrier only for a specific, standardized carrier. The manufacturers regularly require that a hair dye series is matched specifically to the particular needs of certain user groups. This is achieved by adding the corresponding active ingredients or nourishing agents to the standardized carrier. For consumers with severely damaged hair, the addition of one or several nourishing agent(s) with a repairing effect, for example, is recommended; for consumers with fine hair, the addition or one or several active ingredient(s) that strengthen the hair structure is recommended.

However, the result of the dyeing process depends not solely on the combination of OFV and, where applicable DZ, used. It is also influenced by the constituents of the carrier. For example, the addition of nourishing agents and active ingredients to the standardized carriers can lead to a change in the capacity of the dye formed under the influence of the oxidant and/or the partially-oxidizing dye to coat the keratinous fibers and hence to a stronger color change result than that achieved by the standardized carrier.

Such color differences and/or changed color results are described by the present application as "color shift". This color shift, also referred to as dE or ΔE, can be determined by colorimetry by employing a colorimeter, which measures the colors in the L*,a*,b* color space by employing a colorimeter from Datacolor, Type Spectraflash 450, for example.

The L*,a*,b* color space means the CIELAB color space. The L-value denotes the lightness of the color (black-white axis); the higher the value for L, the lighter the color. The a-value denotes the red-green axis of the system; the higher this value, the more the color is shifted into the red. The b-value denotes the yellow-blue axis of the system; the higher this value, the more the color is shifted into the yellow.

The color shift ΔE, i.e. the color difference between two (hair) colors, for which a L*,a*,b* value combination was determined in each case, is calculated according to the following formula:

$$\Delta E = ((L_i - L_0)^2 + (a_i - a_0)^2 + (b_i - b_0)^2)^{1/2}$$

$a_0$, $b_0$ and $L_0$ are the L*, a* and b* values of the hair strands colored using the standardized carrier, whereas $a_i$, $b_i$ and $L_i$ are the L*, a* and b* values, which are obtained for coloration using nourishing agents and/or active ingredients in the standardized carrier. The greater the value for ΔE, the more pronounced the color difference or "color shift". Color differences with an ΔE< about 1 are not perceptible to the human eye. Color differences with an ΔE< about 2 are visible only to the trained eye. Color differences with an ΔE> about 2 are visible even to the untrained eye.

In the worst case, the addition of an additive to a standardized carrier causes a color shift, compared to the standard carrier without additives, of ΔE> about 2, which is visible to even the consumer's untrained eye. To avoid extensive tests with respect to the achievable hair coloration and, where applicable, the fastness properties having to be carried out every time additives are added to standard carriers, it is therefore desirable to identify active ingredients and nourishing agents for the hair, the addition of which causes no or at least only a minimal color shift.

The present disclosure therefore addressed the problem of providing cosmetic agents for changing the color of keratinous fibers, said agents containing one or more selected nourishing agents and active ingredients, which cause no or only a minimal color shift.

BRIEF SUMMARY

It has now unexpectedly emerged that the addition of at least one special hydroxy-terminated, amine-functionalized silicone polymer to cosmetic agents used to color keratinous fibers, more particularly human hair, results in improved nourishment, more particularly to improved combability, with a minimal color shift of $\Delta E<$ about 2, for example of $\Delta E<$ about 1 at the same time.

A first subject matter of the present disclosure is therefore a cosmetic agent for coloring keratin fibers, contained in a suitable cosmetic carrier
a) at least one compound, selected from the group of oxidative dye precursors, partially-oxidative dyes and the mixtures thereof,
b) at least one hydroxy-terminated amine-functionalized silicone polymer of formula (I)

(I)

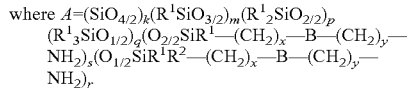

wherein
a denotes integers from 1 to about 20,000, wherein, if a ≥2, the respective values k, m, p, q, s and r in a structural element A can be selected irrespective of previous structural elements A, $R^1$ and $R^2$ denote, independently of one another, hydrogen, a OH group, a linear or branched $C_1$-$C_{12}$-alkyl group, a phenyl group or a vinyl group,
B denotes an oxygen atom, a NH group or sulfur,
x and y denote, independently of one another, integers from 1 to about 10,
t denotes integers from 1 to about 5, and
the total of k+m+p+q+s+r denotes integers from about 3 to about 20,000.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

As contemplated herein, the expression "color change" means the change in the natural color of keratinous fibers, as well as the change in color of already colored keratinous fibers. Said color change can include a lightening, a darkening or a change in shade.

As contemplated herein, the expressions "keratinous fibers and keratin fibers" also mean wool, feathers as well as human hair. According to the present disclosure, a cosmetic means for coloring human hair is exemplary.

According to the present disclosure, the expression "hydroxy-terminated, amine-functionalized silicone polymers" also means silicone polymers having at least one, where applicable protonated, amine group of formula —$NH_2$, as well as being terminated at at least one end of the siloxane backbone by a hydroxy group. Exemplary silicone polymers are terminated at both ends of the siloxane backbone by a hydroxy group.

According to the present disclosure, the term "combability" also means the combability of both wet and dry fibers.

In addition, the expression "fatty alcohols" according to the present disclosure means aliphatic, long-chained, monovalent, primary alcohols, which have unbranched hydrocarbon radicals containing from about 6 to about 30 carbon atoms. The hydrocarbon radicals can be either saturated or mono- or polyunsaturated.

Finally, the expression "fatty acids" according to the present disclosure means aliphatic monocarboxylic acids with unbranched carbon radicals, which have hydrocarbon radicals containing from about 6 to about 30 carbon atoms. The hydrocarbon radicals can be either saturated or mono- or polyunsaturated.

Unless otherwise specified, the total quantity with respect to the components of the cosmetic agent refers to the total quantity of active substance for the respective component. Moreover, unless otherwise specified, the total quantity with respect to the components of the cosmetic agent as contemplated herein refers to the total weight of the oxidant-free cosmetic agent as contemplated herein.

The agents as contemplated herein contain a cosmetic carrier. As contemplated herein, the cosmetically carrier is hydrous, alcoholic or hydrous-alcoholic. According to the present disclosure, creams, emulsions, gels or tenside-containing, foaming solutions for example, such as shampoos, foam aerosols or other preparations suitable for application on the hair, can be used.

As contemplated herein, a hydrous carrier contains at least about 30 wt. %, more particularly at least about 50 wt. %, of water relative to the total weight of the cosmetic agent.

According to the present disclosure, hydrous-alcoholic carriers mean aqueous compositions, containing a $C_1$-$C_4$ alcohol in a total quantity of from about 3 to about 90 wt. %, relative to the total weight of the cosmetic agent, more particularly ethanol and/or isopropanol.

The agents as contemplated herein can additionally contain other organic solvents, such as methoxybutanol, ethyldiglycol, 1,2-propylenglycol, n-propanol, n-butanol, n-butylenglycol, glycerine, diethylenglycolmonoethylether, and diethylenglycolmono-n-butylether. All water-soluble organic solvents are exemplary, wherein the solvent is contained in a total quantity of from about 0.1 to about 30 wt. %, such as from about 1 to about 20 wt. %, for example from about 2 to about 10 wt. %, relative to the total weight of the cosmetic agent.

As a first component, the cosmetic agent as contemplated herein contains a) a chromophoric compound, selected from the group of oxidative dye precursors (OFP), partially-oxidizing dyes (PO) and the mixtures thereof.

In a preferred embodiment, cosmetic agents as contemplated herein contain at least one oxidative dye precursor.

Oxidative dye precursors can be divided into two categories, so-called developer components and coupler components, depending on their reaction behavior. Developer components can combine together to form the actual dye. Therefore, they can be contained in the cosmetic agent as contemplated herein as sole compounds. In an embodiment, the cosmetic agents as contemplated herein therefore contain at least one oxidative precursor of the developer type. Within the scope of the present disclosure, however, it may be that the cosmetic agent as contemplated herein contains at least one oxidative dye precursor of the coupler type. Good results with respect to the coloration of keratin fibers are achieved when the cosmetic agents as contemplated herein contain at least one oxidative dye precursor of the developer type and at least one oxidative dye precursor product of the coupler type.

The developer and coupler components are normally used in a free form. In the case of substances with amino groups, however, use of the salt form thereof, more particularly in the form of hydrochlorides and hydrobromides or sulfates, may be employed.

As contemplated herein, one embodiment employs cosmetic agents which contain the developer and/or coupler components, each in a total quantity of from about 0.001 to about 10 wt. %, for example from about 0.01 to about 8 wt. %, such as from about 0.1 to about 5 wt. %, and in an embodiment from about 0.5 to about 3 wt. %, relative to the total weight of the cosmetic agent.

In another embodiment, the cosmetic agent as contemplated herein is exemplified in that it contains an oxidative dye precursor of the developer and/or coupler components in a total quantity of from about 0.001 to about 10 wt. %, for example from about 0.01 to about 8 wt. %, such as from about 0.1 to about 5 wt. %, and in an embodiment from about 0.5 to about 3 wt. %, relative to the total weight of the cosmetic agent.

Suitable oxidative dye precursors of the developer type are typically p-phenylendiamine and the derivatives thereof. Exemplary p-phenylendiamines are selected from one or several compounds of the group, which is formed from p-phenylendiamine, p-toluylendiamine, 2-chlor-p-phenylendiamine, 2,3-fimethyl-p-phenylendiamine, 2,6-fimethyl-p-phenylendiamine, N,N-bis-(2-hydroxyethyl)-p-phenylen-diamine, 2-(2-hydroxyethyl)-p-phenylendiamine, 2-(1,2-dihydroxyethyl)-p-phenylendiamine, N-(2-hydroxypropyl)-p-phenylendiamine, N-(4'-aminophenyl)-p-phenylendiamine, 2-methoxymethyl-p-phenylendiamine, N-phenyl-p-phenylendiamine, 2-(2-hydroxyethyloxy)-p-phenylendiamine and N-(4-amino-3-methyl-phenyò)-N-[3-(1H-imidazol-1-yl)propyl]amine, as well as the physiologically-tolerable salts thereof.

As contemplated herein, use of compounds containing at least two aromatic rings, which are substituted with amino and/or hydroxyl groups, as the developer components, may be employed. Exemplary two-ring developer components are selected from N,N'-bis-(2-hydroxyethyi)-N,N'-bis-(4'-aminophenyl)-1,3-diaminopropan-2-ol, N,N'-bis-(4-aminophenyl)-1,4-diazacycloheptane, bis-(2-hydroxy-5-aminophenyl)methane, as well as the physiologically-tolerable salts thereof.

As contemplated herein, use of a p-aminophenol derivative or one of the physiologically-tolerable salts thereof as the developer component, may also be employed. Exemplary p-aminophenols are p-aminophenol, N-methyl-p-aminophenol, 4-amino-3-methylphenol, 4-amino-2-aminomethyl-phenol, 4-amino-2-(1,2-dihydroxyethyl)phenol, 4-amino-2-(diethylaminomethyl)phenol, as well as the physiologically-tolerable salts thereof.

The developer components can also be selected from o-aminophenol and the derivatives thereof, preferred from 2-amino-4-methylphenol, 2-amino-5-methylphenol, 2-amino-4-chlorphenol and/or the physiologically-tolerable salts thereof.

Moreover, the developer components can be selected from heterocyclic developer components, such as pyrimidine derivatives, pyrazole derviatives, pyrazolopyrimidine derivatives and/or the physiologically-tolerable salts thereof. Exemplary pyrimidine derivatives are 2,4,5,6-tetraaminopyrimidine, 4-hydroxy-2,5,6-triaminopyrimidine and the physiologically-tolerable salts thereof. An exemplary pyrazole derivative is 4,5-diamino-1-(2-hydroxyethyl) pyrazole, as well as the physiologically-tolerable salts thereof. Pyrazolo[1,5-a]pyrimidine is an exemplary pyrazolopyrimidines.

Exemplary oxidative dye precursors of the developer type are selected from the group of p-phenylendiamine, p-toluylendiamine, 2-(2-hydroxyethyl)-p-phenylendiamine, 2-(1,2-dihydroxyethyl)-p-phenylendiamine, N,N-bis-(2-hydroxyethyl)-p-phenylendiamine, 2-methoxymethyl-p-phenylendiamine, N-(4-amino-3-methylphenyl)-N-[3-(1H-imidazol-1-yl)propyl]amine, N,N'-bis-(2-hydroxy-ethyl)-N,N'-bis-(4-aminophenyl)-1,3 -diamino-propan-2-ol, bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7, 10-tetraoxadecan, p-aminophenol, 4-amino-3-methylphenol, 4-amino-2-amino-methylphenol, 4-amino-2-(1,2-dihydroxyethyl)phenol and 4-amino-2-(diethylaminomethyl)phenol, 4,5-aiamino-1-(2-hydroxyethyl)pyrazole, 2,4,5,6-tetraamino-pyrimidine, 4-hydroxy-2,5,6-triaminopyrimidine, 2-hydroxy-4,5,6-triaminopyrimidine or the physiologically-tolerable salts thereof.

Exemplary developer components are p-toluylendiamine, 2-(2-hydroxyethyl)-p-phenylen-diamine, 2-methoxymethyl-p-phenylendiamine, N-(4-amino-3-methylphenyl)-N-[3-(1H-imidazol-1-yl)-propyl)amine, and/or 4,5-diamino-1-(2-hydroxyethyl)pyrazole, as well as the physiologically-tolerable salts thereof.

According to another embodiment of the present disclosure, the cosmetic agent as contemplated herein contains, as oxidative dye precursors, at least one coupler component in addition to at least one developer component. m-phenylendiamine derivatives, naphthols, resorcin and resorcin derivatives, pyrazolones and m-aminophenol derivatives are typically used as coupler components.

Exemplary coupler components as contemplated herein are selected from:

(A) m-aminophenol and the derivatives thereof, more particularly 3-aminophenol, 5-amino-2-methylphenol, 3-amino-2-chlor-6-methylphenol, 5-amino-4-chlor-2-methylphenol, 5-(2'-hydroxyethyl)-amino-2-methylphenol and 2,4-dichlor-3-aminophenol, (B) o-aminophenol and the derivatives thereof, such as 2-amino-5-ethylphenol, (C) m-diaminobenzol and the derivatives thereof, such as 2,4-diaminophenoxy-ethanol, 1,3-bis-(2',4'-diaminophenoxy)-propane, 1-methoxy-2-amino-4-(2'-hydroxyethylamino)benzol, 2,6-bis-(2'-hydroxyethylamino)-1-methylbenzol, 2-({3-[(2-Hydroxyethyl)amino]-4-methoxy-5-methylphenyl}amino)ethanol and 2-({3-[(2-hydroxyethyl)amino]-2-methoxy-5-methylphenyl}-amino)ethanol, (D) o-diaminobenzol and the derivatives thereof, (E) di and/or trihydroxybenzol derivatives, more particularly resorcin, 2-chlorresorcin, 4-chlorresorcin, 2-methylresorcin and 1,2,4-trihydroxybenzol, (F) pyridine derivatives, more particularly 3-amino-2-methylamino-6-methoxypyridine, 2,6-diamino pyridine, 2,6-dihydroxy-3,4-dimethylpyridine, 2-amino-3-hydroxypyridine and 3,5-diamino-2,6-dimethoxy-pyridine, (G) naphthaline derivatives, such as 1-naphthol and 2-methyl-1-naphthol, (H) morpholine derivatives, such as 6-hydroxybenzomorpholine, (I) quinolaxine derivatives,
(J) pyrazol derivatives, such as 1-phenyl-3-methylpyrazol-5-on,
(K) indol derivatives, such as 6-hydroxyindol,
(L) pyrimidine derivatives of
(M) methylendioxybenzol derivatives, such as 1-(2'-hydroxyethyl)-amino-3,4-methylene dioxybenzol, as well as the physiologically-tolerable salts thereof.

Coupler components as contemplated herein are selected from the group, which is formed from 3 -aminophenol, 5 -amino-2-methylphenol, 3-amino-2-chlor-6-methyl phenol, 2-hydroxy-4-aminophenoxyethanol, 5-amino-4-chlor-2-methylphenol, 5-(2-hydroxyethyl)-amino-2-methyl phenol, 2,4-dichlor-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxyethylamino)benzol, 1,3-bis(2,4-diaminophenyl)propane, 2,6-bis(2'-hydroxyethylamino)-1-methylbenzol, 2-({3-[(2-hydroxyethyl)amino]-4-methoxy-5-methylphenyl}amino) ethanol, 2-({3-[(2-hydroxyethyl) amino]-2-methoxy-5-methylphenyl}amino)ethanol, 2-({3-[(2-hydroxyethyl) amino]-4,5-dimethylphenyl}amino)ethanol, 2-[3-morpholine-4-ylphenyl)amino]ethanol, 3-amino-4-(2-methoxy-ethoxy)-5-methylphenylamine, 1-amino-3-bis-(2-hydroxyethyl)aminobenzol, resorcin, 2-methylresorcin, 4-chlorresorcin, 1,2,4-trihydroxybenzol, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-on, 1-naphthol, 1,5-dihydroxynaphthaline, 2,7-dihydroxynaphthaline, 1,7-dihydroxynaphthaline, 1,8-dihydroxynaphthaline, 4-hydroxyindole, 6-hydroxyindole, 7-hydroxyindole, 4-hydroxyindoline, 6-hydroxyindoline, 7-hydroxyindoline or the physiologically-tolerable salts of the aforementioned compounds.

Exemplary coupler components as contemplated herein are resorcin, 2-methylresorcin, 5-amino-2-methylphenol, 3-aminophenol, 2-(2,4-diaminophenoxy)ethanol, 1,3-bis-(2,4-diamino-phenoxy)propane, 1-methoxy-2-amino-4-(2'-hydroxyethylamino)benzol, 2-amino-3-hydroxypyridine, 2,6-dihydroxy-3,4-dimethylpyridine, 1,5-dihydroxynaphthaline, 2,7-dihydroxynaphthaline and 1-naphthol, as well as the physiologically-tolerable salts thereof.

In an embodiment of the present disclosure, the cosmetic agents as contemplated herein are exemplified in that they contain at least one developer component, selected from the group of p-phenylendiamine, p-toluylendiamine, N,N-bis-(2-hydroxyethyl)amino-p-phenylendiamine, 1,3-bis-[(2-hydroxyethyl-4'-aminophenyl)amino]-propan-2-ol, 1,10-bis-(2',5'-diaminophenyl)-1,4,7,10-tetraoxadecane 4-aminophenol, 4-amino-3 -methylphenole, bis-(5-amino-2-hydroxyphenyl)methane, 2,4,5,6-tetraaminopyrimidine, 2-hydroxy-4,5,6-triaminopyrimidine, 4,5-diamino-1-(2-hydroxyethyl)-pyrazole, the physiologically-tolerable salts thereof and the mixtures thereof, and at least one coupler component, selected from the group of resorcin, 2-methylresorcin, 5-methylresorcin, 2,5-dimethylresorcin, 4-clorresorcin, resorcin monomethylether, 5-aminophenole, 5-amino-2-methylphenole5-2-hydroxyethyl)amino-2-methylphenol, 3-amino-4-chlor-2-methylphenole, 3-amino-2-chlor-6-methylphenole, 3-amino-2,4-dichlorphenole, 2,4-diaminophenoxyethanol, 2-amino-4-(2-hydroxyethyl)amino-anisolsulfate, 1,3-bis-(2,4-diaminophenoxy)propane, 2-amino-3-hydroxypyridine, 2-methylamino-3-amino-6-methoxypyridine, 2,6-dihydroxy-3,4-dimethylpyridine, 3,5-diamino-2,6-dimethoxypyridine, 1-naphthol, 2-methyl-1-naphthol, 1,5-dihydroxynaphthaline, 2,7-dihydroxynaphthaline, 1-phenyl-3-methylpyrazol-5-on, 2,6-bis-[(2-hydroxyethyl)amino]-toluol, 4-hydroxyindol, 6-hydroxyindol, 6-hydroxybenzomorpholine, the physiologically-tolerable salts thereof and the mixtures thereof.

The present disclosure may specify that the cosmetic agents as contemplated herein additionally contains at least one partially-oxidizing dye. Partially-oxidizing dyes are dyes that coat the substrate itself and do not require an oxidative process to create the color. Partially-oxidizing dyes are usually nitrophenylendiamines, nitroaminophenols, azo dyes, anthrachinones or indophenols.

Partially-oxidizing dyes can be sub-divided into anionic, cationic and non-ionic partially-oxidizing dyes.

Cosmetic agents are exemplified in that they contain at least one partially-oxidizing dye, which is selected from the group of nitrophenylendiamines, nitroaminophenols, azo dyes, anthrachinons or indophenols, for example from the group of dyes known under the international designations and/or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzol, 2-amino-4-nitrophenol, 1,4-bis-(β-hydroxyethyl)-amino-2-nitrobenzol, 3-nitro-4-(β-hydroxyethyl)-aminophenol, 2-(2'-hydroxyethyl)amino-4,6-dinitrophenol, 1-(2'-hydroxyethyl)amino-4-methyl-2-nitrobenzol, 1-amino-4-(2'-hydroxyethyl)-amino-5-chlor-2-nitrobenzol, 4-amino-3-nitrophenol, 1-(2'-ureidoethyl)amino-4-nitrobenzol, 4-amino-2-nitrodiphenylamine-2'-carboxylic acid, 6-nitro-1,2,3,4-tetrahydrochinoxaline, 2-Hydroxy-1,4-naphthochinon, pikramic acid and the salts thereof, 2-amino-6-chloro-4-nitrophenol, 4-ethylamino-3-nitrobenzoic acid and 2-chloro-6-ethylamino-1-hydroxy-4-nitrobenzol.

Moreover, partially-oxidizing dyes that occur in nature, such as Henna red, Henna neutral, Henna black, chamomile blossoms sandalwood, black tea, walnut, Cascara bark, sage, logwood, madder root, catechu, ceder and alkanna root, can also be used.

As contemplated herein, one embodiment is for cosmetic agents containing at least one partially-oxidizing agent in a total quantity of from about 0.001 to about 10 wt. %, for example from about 0.01 to about 8 wt. %, such as from about 0.1 to about 5 wt. %, and in one embodiment from about 0.5 to about 3 wt. %, relative to the total weight of the cosmetic agent.

The cosmetic agents as contemplated herein may contain as a second component at least one special hydroxy-terminated, amine-functionalized silicone polymer. The addition of said silicone polymer leads to improved nourishment, more particularly wet combability without, however, causing a color shift that is visible to the human eye, i.e. the color change ΔE caused by the addition of special silicone polymers is less than 2, more particularly less than 1.

As contemplated herein, it has proven advantageous for radicals $R^1$ and B to denote specific groups in formula (I). Therefore, it is exemplary for radical le to denote a methyl group and B to denote a NH group in formula (I).

According to the present disclosure, it is also exemplary for the hydroxy-terminated, amine-functionalized silicone polymer of formula (I) to contain a specific number of OH groups and to be provided with a specific amine function. Some embodiments of the present disclosure are therefore exemplified in that formula (I) x denotes the integer 3, y denotes the integer 2 and t denotes integers 1 or 2.

According to the present disclosure, good results are obtained if the silicone polymer of formula (I) contains special siloxane units, as well as specific siloxanes functionalized with amine groups. In this context, silicone polymers of formula (I) being terminated at both ends of the siloxane backbone by a hydroxy group are exemplary. According to the present disclosure, a hydroxy-terminated, amine-functionalized silicone polymer of formula (Ia) may be used as the hydroxy-terminated, amine-functionalized silicone polymer of formula (I)

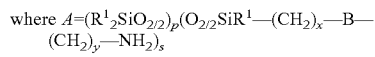

wherein
a denotes integers from 1 to about 1,000, wherein, if a ≥2, the respective values p and s in a structural element A can be selected irrespective of previous structural elements A,
$R^1$ denotes a methyl group,
B denotes a NH group,
x denotes the integer 3,
y denotes the integer 2,
t denotes integers 1 or 2, more particularly the integer 2,
p denotes integers from about 8 to about 1,000, and
s denotes integers from 1 to about 800.

Use of the aforementioned hydroxy-terminated, amino-functionalized silicone polymers of formula (Ia) in cosmetic agents for dyeing keratinous fibers leads to a relatively high nourishing effect, more particularly to relatively good wet combability, with only a relatively minimal color shift of ΔE less than about 2, such as less than about 1, at the same time.

According to the present disclosure, however, it can also be possible to use silicone polymers of formula (I), which are terminated only at one end of the silicone backbone with a hydroxy group, and at the other end of the siloxane backbone with an amine group. These embodiments are exemplified in that a hydroxy-terminated, amine-functionalized silicone polymer of formula (Ib) is used as the hydroxy-terminated, amine-functionalized silicone polymer of formula (I)

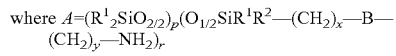

wherein
a denotes integers from 1 to about 1,000, wherein, if a ≥2, the respective values p and r in a structural element A can be selected irrespective of previous structural elements A,
$R^1$ and $R^2$ each denote a methyl group,
B denotes a NH group,
x denotes the integer 3,
y denotes the integer 2,
t denotes integers 1 or 2, more particularly the integer 1,
p denotes integers from about 8 to about 1,000, and
a denotes integers from 1 to about 800.

Use of the aforementioned hydroxy-terminated, amino-functionalized silicone polymers of formula (Ib) in cosmetic agents for dyeing keratinous fibers leads to a relatively high nourishing effect, more particularly to relatively good wet combability, with only a relatively minimal color shift of ΔE less than about 2, such as less than about 1, at the same time. As contemplated herein, it can be desirable for the cosmetic agents to contain at least one silicone polymer of formula (Ia) and at least one silicone polymer of formula (Ib) as the hydroxy-terminated, amine-functionalized silicone polymer of formula (I).

As contemplated herein, it can be desirable for at least one hydroxy-terminated, amine-functionalized silicone polymer b) to be used in specific quantity ranges. Exemplary embodiments of the cosmetic agents as contemplated herein are exemplified in that the cosmetic agent contains the at least one silicone block copolymer b) in a total quantity of from about 0.0001 to about 20 wt. %, such as from about 0.0005 to about 10 wt. %, for example from about 0.005 to about 8.0 wt. %, and in one embodiment from about 0.01 to about 5.0 wt. %, and in another embodiment from about 0.1 to about 1.0 wt. %, relative to the total weight of the cosmetic agent. The specified total quantities refer to the total quantity of hydroxy-terminated, amine-functionalized silicone polymers of formula (I) and/or formula (Ia) and/or formula (Ib). Use of the aforementioned total quantity of the special hydroxy-terminated, amine-functionalized silicone polymer leads to increased nourishment of the keratinous fibers without, however, the color result being influenced in the form of a visible color shift.

It has emerged that the addition of polyoxyethylen(10)-tridecylether can stabilize the at least one hydroxy-terminated, amine-functionalized silicone polymer, more particularly the hydroxy-terminated, amine-functionalized silicone polymers of formulas (Ia) and/or (Ib), in the cosmetic agents as contemplated herein, thereby increasing the nourishing effect. Cosmetic agents as contemplated herein therefore contain in addition polyoxyethylen(10)-tridecylether in a total quantity of from about 0.00001 to about 1.0 wt. %, for example from about 0.0005 to about 0.8 wt. %, such as from about 0.001 to about 0.5 wt. %, and in one embodiment from about 0.01 to about 0.4 wt. %, and in another embodiment from about 0.1 to about 0.3 wt. %, relative to the total weight of the cosmetic agent.

The cosmetic agents as contemplated herein can contain other active ingredients and additive. According to the present disclosure, it is therefore exemplary for the cosmetic agent to contain in addition at least one other compound, selected from the group of (i) thickening agents; (ii) linear or branched, saturated or unsaturated alcohols with 8 to 20 carbon atoms; (iii) tensides, such as amphoteric tensides; (iv) alkalizing agents; (v) oils, as well as (vi) the mixtures thereof.

In some embodiments, the cosmetic agents as contemplated herein are formulated as free-flowing preparations. The cosmetic agents may be formulated in such a manner that they can be readily applied and distributed at the place of use on the one hand, but on the other are adequately viscous such that they remain at the site of action and do not run (or substantially avoid running) during the exposure time.

It has proven advantageous according to the present disclosure for the cosmetic agent as contemplated herein to contain at least one thickening agent from the group of (i) anionic, synthetic polymers; (ii) cationic, synthetic polymers; (iii) naturally occurring thickening agents, such as non-ionic guar gums, scleroglucan gums or xanthan gums, rummi arabicum, Ghatti rubber, Karaya rubber, Tragant rubber, Carrageen rubber, Agar-Agar, locust bean gum, pectins, alginates, starch fractions and derivatives, such as amylose, amylopectin and dextrins, as well as cellulose derivatives, such as methyl cellulose, carboxyalkyl celluloses and hydroxyalkyl celluloses; (iv) non-ionic synthetic polymers, such as polyvinyl alcohol or polyvinylpyrrolidinon; (v) inorganic thickening agents, for example phyllosilicates, such as bentonit, more particularly smektites, such as montmorillonite or hectorit; as well as (vi) the mixtures thereof, in a total quantity of from about 0.0005 to about 5.0 wt. %, for example from about 0.001 to about 3.0 wt. %, such as from about 0.005 to about 1.0 wt. %, and in one embodiment from about 0.008 to about 0.01 wt. %, relative to the total weight of the cosmetic agent.

In this context, one embodiment may include at least one naturally occurring thickening agent, for example xanthan gum, as well as the salts thereof, to be contained, as the thickening agent, in a total quantity of from about 0.0005 to about 5.0 wt. %, for example from about 0.001 to about 1.0 wt. %, such as from about 0.005 to about 1.0 wt. %, and in one embodiment from about 0.01 to about 0.1 wt. %, relative to the total weight of the cosmetic agent.

According to the present disclosure, it can be possible for the linear or branched, saturated or unsaturated alcohol with 8 or 20 carbon atoms to be selected from the group of myristyl alcohol (1-tetradecanol), stearyl alcohol (1-octadecanol), cetearyl alcohol, 2-octyldodecanol, arachyl alcohol (eicosan-1-ol), gadoleyl alcohol ((9Z)-eicos-9-en-1-ol), arachidon alcohol ((5Z, 8Z, 11Z, 14Z)-eicosa-5,8,11,14-tetraen-1-ol), preferably 2-octyldodecanol and/or cetearyl alcohol, and in a total quantity of from about 1.0 to about 35 wt. %, for example from about 5.0 to about 30 wt. %, such as from about 10 to about 25 wt. %, and in one embodiment from about 12 to about 20 wt. %, relative to the total weight of the cosmetic agent.

In some embodiments, the cosmetic agents as contemplated herein can also contain at least one partial ester from a polyol with from about 2 to about 6 carbon atoms and linear saturated carbon atoms with from about 12 to about 30, more particularly from about 14 to about 22 carbon atoms, wherein the partial ester can be hydroxylated, in a total quantity of from about 0.5 to about 10 wt. %, for example from about 3.0 to about 8.0 wt. %, relative to the total weight of the cosmetic agent. The partial esters may be the mono and diesters of glycerine or the monoesters of propylenglycol or the mono and diesters of ethylenglycol or the mono, di, tri and tetraesters of pentaerythrit, each with linear saturated $C_{12}$-$C_{30}$ carboxylic acids, which can be hydroxylated, more particularly those with palmitic and stearic acids, the sorbitanmono-, -di- or -triesters of linear saturated $C_{12}$-$C_{30}$ carboxylic acids, which can be hydroxylated, for example those of myristin acids, palmitic acids, stearic acids or of mixtures of said fatty acids and the methylglucosemono- and diesters of linear saturated $C_{12}$-$C_{30}$ carboxylic acids, which can be hydroxylated.

According to the present disclosure, the cosmetic agent as contemplated herein can contain at least one polyolpartial ester, selected from glycerine monostearate, glycerin monopalmitate, glycerin distearate, glycerin dipalmitate, ethylenglycol monostearate, ethylenglycolmono palmitate, ethylenglycol distearate, ethylenglycoldipalmitate, as well as the mixtures thereof, for example mixtures from glycerin-monostearate, glycerinmonopalmitate, glycerindistearate and glycerindipalmitate in a total quantity of from about 0.5 to about 10 wt. %, for example from about 3.0 to about 8.0 wt. %, relative to the total weight of the cosmetic agent.

The use of the aforementioned alcohols, partial esters and poly-partial esters in the cosmetic agent as contemplated herein can be suitable if the cosmetic agent as contemplated herein exists in the form of a creamy oil-in-water emulsion.

According to the present disclosure, the cosmetic agent as contemplated herein can also contain at least one tenside. Tensides according to the present disclosure are amphiphilic (bifunctional) compounds, which consist of at least one hydrophobic and at least one hydrophilic molecular part. Some properties of tensides and emulsifiers are the absorption oriented to boundary surfaces, as well as the aggregation to micelles and the formation of lyotropic phases.

According to an exemplary embodiment of the present disclosure, the cosmetic agents as contemplated herein contain at least one amphoteric tenside in a total quantity of from about 0.1 to about 5.0 wt. %, for example from about 0.2 to about 2.0 wt. %, relative to the total weight of the cosmetic agent. Amphoteric and/or zwitterionic tensides are surfactants having at least one quarternary ammonium group and at least one -GOQ$^{(-)}$- or -803$^{(-)}$ group.

According to the present disclosure, the compounds below are exemplary amphoteric tensides:

Alkylbetains having from about 8 to about 20 carbon atoms in the alkyl group,

Amidopropylbetaines having from about 8 to about 20 carbon atoms in the acyl group, sulfobetains having from about 8 to about 20 carbon atoms in the acyl group and amphoacetates or amphodiacetates having from about 8 to about 20 carbon atoms in the acyl group.

In one embodiment, the cosmetic agents as contemplated herein contain as tenside at least one amphoteric tenside, selected from amidopropylbetaines with from about 9 to about 13 carbon atoms in the acyl group, in a total quantity of from about 0.1 to about 5.0 wt. %, for example from about 0.2 to about 2.0 wt. %, relative to the total weight of the cosmetic agent.

The cosmetic agents as contemplated herein can also contain at least one ethoxylated non-ionic tenside in a total quantity of from about 0.5 to about 6.0 wt. %, for example from about 1.0 to about 4.0 wt. %, relative to the total weight of the cosmetic agent. It has proven desirable for the ethoxylated non-ionic tenside to have a HLB value of above 10, for example above 13. This may require that the non-ionic tenside has an adequately high degree of ethoxylation. In this context, the cosmetic agent as contemplated herein therefore contains at least one ethoxylated tenside having at least about 12 ethylene oxide units as the ethoxylated non-ionic tenside. In addition to the correspondingly ethoxylated fatty alcohols, for example lauryl alcohol, myristyl alcohol, cetyl alcohol, stearyl alcohol, arachylalcohol and behenyl alcohol, the present disclosure provides that the sediments of from about 20 to about 60 mol of ethylenoxide for castor oil and hydrogenated castor oil are particularly suitable. The at least one ethoxylated non-ionic tenside may be selected from tensides with the INGI designation ceteth-12, steareth-12, ceteareth-12, ceteth-20, steareth-20, ceteareth-20, ceteth-30, steareth-30, cetea-reth-30, oleth-30, ceteareth-50, PEG-40 hydrogenated castor oil and PEG-60 hydrogenated castor oil, as well as mixtures of said substances, for example selected from ceteth-20, steareth-20, ceteareth-20, ceteth-30, steareth-30 and ceteareth-30.

According to the present disclosure, cosmetic agents may have an alkaline pH value, for example between about pH 8.0 and about pH 12, such as between about pH 9.0 to about pH 11. These pH values are desirable to provide an opening of the external cuticle layer (cuticula) and facilitate a penetration of oxidative dye precursors and/or of the oxidant into the hair.

The aforementioned pH value may be set using at least one alkalizing agent. According to the present disclosure, the alkalizing agent may be selected from the group of (i) inorganic alkalizing agents; (ii) organic alkalizing agents; as well as (iii) the mixtures thereof, and in a total quantity of from about 1.5 to about 9.5 wt. %, for example from about 2.5 to about 8.5 wt. %, such as from about 3.0 to about 8.0 wt. %, and in one embodiment from about 3.5 to about 7.5 wt. %, relative to the total weight of the cosmetic agent.

Exemplary inorganic alkalizing agents are selected from the group formed from ammoniac and/or ammonium hydroxide, i.e. hydrous solutions of ammoniac, sodium hydroxide, potassium hydroxide, calcium hydroxide, barium hydroxide, sodium phosphate, potassium phosphate, sodium silicate, potassium silicate, sodium carbonate and potassium carbonate, as well as mixtures thereof. Ammonia and/or ammonium hydroxide is a suitable alkalizing agent. Ammonia is suitable in a total quantity of from about 0.1 to about 20 wt. %, for example from about 0.5 to about 10 wt. %, such as from about 1.0 to about 7.0 wt. %, relative to the total weight of the cosmetic agent.

Exemplary organic alkalizing agents are selected from at least one alkanolamine. Alkanolamines as contemplated herein are selected from alkanolamines from primary, secondary or tertiary amines with a C2-C6-alkyl base body, which carries at least one hydroxyl group. Suitable alkanolamines are selected from the group formed from 2-aminoethan-1-ol (monoethanolamine), 3-aminoprop an-1-ol, 4-amino-butan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methyl-propanol, 2-amino-2-methylbutanol, 3-amino-2-methylpropan-1-ol, 1-amino-2-methylpropan-2-ol, 3 aminopropan 1,2-diol, 2-amino-2-methylpropan,3-diol, 2-amino-2-ethyl-1,3-propanediol, N,N-dimethyl-ethanolamine, triethanolamine, diethanolamine and triisopropanolamine. For example, alkanolamines as contemplated herein are selected from the group of 2-aminoethan-1-ol (monoethanolamine), 2-amino-2-methylpropan-1-ol, 2-amino-2-methyl-propan-1,3-diol and triethanolamine. In some embodiments, cosmetic agents as contemplated herein contain a mixture of Mono-ethanolamine and 2-amino-2-methylpropan-1ol. It is exemplary for the at least one alkanolamine to be contained in a total quantity of from about 0.05 to about 15 wt. %, for example from about 0.5 to about 10 wt. %, such as from about 3.5 to about 7.5 wt. %, relative to the total weight of the cosmetic agent.

Other organic alkalizing agents as contemplated herein are selected from alkali amino acids, for example selected from the group formed from L-arginin, D-arginin, D/L-arginin, L-lysin, D-lysin, D/L-lysin, as well as the mixtures thereof. Suitable alkaline amino acids as contemplated herein are selected from L-arginine, D-arginine and D/L-arginine. Suitable cosmetic agents as contemplated herein contain at least one alkalizing agent that differs from alkanolamines and ammoniac in a total quantity of from about 0.05 to about 5.0 wt. %, for example from about 0.5 to about 3.0 wt. %, relative to the total weight of the cosmetic agent.

In one embodiment, the cosmetic agents as contemplated herein contain, as the alkalizing agent, a mixture of at least two different alkanolamines, for example monoethanolamine and 2-amino-2-methylpropan-1-ol, in a total quantity of from about 0.05 to about 15 wt. %, for example from about 0.5 to about 10 wt. %, such as from about 3.5 to about 7.5 wt. %, relative to the total weight of the cosmetic agent.

In some embodiments, the pH value of the cosmetic agent as contemplated herein, measured at 22° C., is from about 8 to about 13, for example from about 9.5 to about 12, such as from about 10 to about 11.5, and in one embodiment from about 10.5 to about 11.

According to the present disclosure, it can also be suitable for the cosmetic agent to contain at least one oil, selected from the group of sunflower oil, corn oil, soy oil, pumpkin seed oil, grape seed oil, sesame oil, hazelnut oil, apricot seed oil, macadamia nut oil, arara oil, castor oil, avocado oil, as well as the mixtures thereof, in a total quantity of from about 0.1 to about 10 wt. %, for example from about 0.2 to about 5.0 wt. %, such as from about 0.5 to about 2.0 wt. %, relative to the total weight of the cosmetic agent. The use of at least one of the aforementioned oils may increase the nourishing effect of the hydroxy-terminated, amine-functionalized silicone polymers.

The cosmetic agent as contemplated herein may contain grape seed oil in a total quantity of from about 0.1 to about 10 wt. %, for example from about 0.2 to about 5.0 wt. %, such as from about 0.5 to about 2.0 wt. %, relative to the total weight of the cosmetic agent.

The table below shows embodiments AF 1 to AF 96 of the cosmetic agent as contemplated herein (all values in wt. %, unless otherwise stated):

|  | AF 1 | AF 2 | AF 3 | AF 4 |
|---|---|---|---|---|
| Chromophoric compound | 0.001-10 | 0.01-8.0 | 0.1-5.0 | 0.5-3.0 |
| Silicone polymers of formula (I) | 0.001-5.0 | 0.05-4.0 | 0.5-3.0 | 1.0-2.0 |
| Cosmetic carrier[1] | Ad 100 | Ad 100 | Ad 100 | Ad 100 |

|  | AF 5 | AF 6 | AF 7 | AF 8 |
|---|---|---|---|---|
| Chromophoric compound[2] | 0.001-10 | 0.01-8.0 | 0.1-5.0 | 0.5-3.0 |
| Silicone polymers of formula (I) | 0.001-5.0 | 0.05-4.0 | 0.5-3.0 | 1.0-2.0 |
| Cosmetic carrier[1] | Ad 100 | Ad 100 | Ad 100 | Ad 100 |

|  | AF 9 | AF 10 | AF 11 | AF 12 |
|---|---|---|---|---|
| Chromophoric compound | 0.001-10 | 0.01-8.0 | 0.1-5.0 | 0.5-3.0 |
| Silicone polymer of formula (I)[3] | 0.001-5.0 | 0.05-4.0 | 0.5-3.0 | 1.0-2.0 |
| Cosmetic carrier[1] | Ad 100 | Ad 100 | Ad 100 | Ad 100 |

|  | AF 13 | AF 14 | AF 15 | AF 16 |
|---|---|---|---|---|
| Chromophoric compound[2] | 0.001-10 | 0.01-8.0 | 0.1-5.0 | 0.5-3.0 |
| Silicone polymer of formula (I)[3] | 0.001-5.0 | 0.05-4.0 | 0.5-3.0 | 1.0-2.0 |
| Cosmetic carrier[1] | Ad 100 | Ad 100 | Ad 100 | Ad 100 |

-continued

|  | AF 17 | AF 18 | AF 19 | AF 20 |
|---|---|---|---|---|
| Chromophoric compound | 0.001-10 | 0.01-8.0 | 0.1-5.0 | 0.5-3.0 |
| Silicone polymer of formula (Ia) | 0.001-5.0 | 0.05-4.0 | 0.5-3.0 | 1.0-2.0 |
| Cosmetic carrier[1] | Ad 100 | Ad 100 | Ad 100 | Ad 100 |

|  | AF 21 | AF 22 | AF 23 | AF 24 |
|---|---|---|---|---|
| Chromophoric compound[2] | 0.001-10 | 0.01-8.0 | 0.1-5.0 | 0.5-3.0 |
| Silicone polymer of formula (Ia) | 0.001-5.0 | 0.05-4.0 | 0.5-3.0 | 1.0-2.0 |
| Cosmetic carrier[1] | Ad 100 | Ad 100 | Ad 100 | Ad 100 |

|  | AF 24 | AF 26 | AF 27 | AF 28 |
|---|---|---|---|---|
| Chromophoric compound | 0.001-10 | 0.01-8.0 | 0.1-5.0 | 0.5-3.0 |
| Silicone polymer of formula (Ib) | 0.001-5.0 | 0.05-4.0 | 0.5-3.0 | 1.0-2.0 |
| Cosmetic carrier[1] | Ad 100 | Ad 100 | Ad 100 | Ad 100 |

|  | AF 29 | AF 30 | AF 31 | AF 32 |
|---|---|---|---|---|
| Chromophoric compound[2] | 0.001-10 | 0.01-8.0 | 0.1-5.0 | 0.5-3.0 |
| Silicone polymer of formula (Ib) | 0.001-5.0 | 0.05-4.0 | 0.5-3.0 | 1.0-2.0 |
| Cosmetic carrier[1] | Ad 100 | Ad 100 | Ad 100 | Ad 100 |

|  | AF 33 | AF 34 | AF 35 | AF 36 |
|---|---|---|---|---|
| Chromophoric compound[2] | 0.001-10 | 0.01-8.0 | 0.1-5.0 | 0.5-3.0 |
| Silicone polymer of formulas (Ia) and (Ib) | 0.001-5.0 | 0.05-4.0 | 0.5-3.0 | 1.0-2.0 |
| Cosmetic carrier[1] | Ad 100 | Ad 100 | Ad 100 | Ad 100 |

|  | AF 37 | AF 38 | AF 39 | AF 40 |
|---|---|---|---|---|
| Chromophoric compound | 0.001-10 | 0.01-8.0 | 0.1-5.0 | 0.5-3.0 |
| Silicone polymer of formula (Ia) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Cosmetic carrier[1] | Ad 100 | Ad 100 | Ad 100 | Ad 100 |

|  | AF 41 | AF 42 | AF 43 | AF 44 |
|---|---|---|---|---|
| Chromophoric compound[2] | 0.001-10 | 0.01-8.0 | 0.1-5.0 | 0.5-3.0 |
| Silicone polymer of formula (Ia) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Cosmetic carrier[1] | Ad 100 | Ad 100 | Ad 100 | Ad 100 |

|  | AF 45 | AF 46 | AF 47 | AF 48 |
|---|---|---|---|---|
| Chromophoric compound | 0.001-10 | 0.01-8.0 | 0.1-5.0 | 0.5-3.0 |
| Silicone polymer of formula (Ib) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Cosmetic carrier[1] | Ad 100 | Ad 100 | Ad 100 | Ad 100 |

|  | AF 49 | AF 50 | AF 51 | AF 52 |
|---|---|---|---|---|
| Chromophoric compound[2] | 0.001-10 | 0.01-8.0 | 0.1-5.0 | 0.5-3.0 |
| Silicone polymer of formula (Ib) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Cosmetic carrier[1] | Ad 100 | Ad 100 | Ad 100 | Ad 100 |

|  | AF 53 | AF 54 | AF 55 | AF 56 |
|---|---|---|---|---|
| Chromophoric compound[2] | 0.001-10 | 0.01-8.0 | 0.1-5.0 | 0.5-3.0 |
| Silicone polymer of formulas (Ia) and (Ib) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Cosmetic carrier[1] | Ad 100 | Ad 100 | Ad 100 | Ad 100 |

|  | AF 57 | AF 58 | AF 59 | AF 60 |
|---|---|---|---|---|
| Chromophoric compound | 0.001-10 | 0.01-8.0 | 0.1-5.0 | 0.5-3.0 |
| Silicone polymer of formula (Ia) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Alkalizing agent[4] | 0.05-15 | 0.5-10 | 1.5-8.0 | 3.5-7.5 |
| Cosmetic carrier[1] | Ad 100 | Ad 100 | Ad 100 | Ad 100 |

-continued

|  | AF 61 | AF 62 | AF 63 | AF 64 |
|---|---|---|---|---|
| Chromophoric compound[2] | 0.001-10 | 0.01-8.0 | 0.1-5.0 | 0.5-3.0 |
| Silicone polymer of formula (Ia) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Alkalizing agent[4] | 0.05-15 | 0.5-10 | 1.5-8.0 | 3.5-7.5 |
| Cosmetic carrier[1] | Ad 100 | Ad 100 | Ad 100 | Ad 100 |

|  | AF 65 | AF 66 | AF 67 | AF 68 |
|---|---|---|---|---|
| Chromophoric compound | 0.001-10 | 0.01-8.0 | 0.1-5.0 | 0.5-3.0 |
| Silicone polymer of formula (Ib) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Alkalizing agent[4] | 0.05-15 | 0.5-10 | 1.5-8.0 | 3.5-7.5 |
| Cosmetic carrier[1] | Ad 100 | Ad 100 | Ad 100 | Ad 100 |

|  | AF 69 | AF 70 | AF 71 | AF 72 |
|---|---|---|---|---|
| Chromophoric compound[2] | 0.001-10 | 0.01-8.0 | 0.1-5.0 | 0.5-3.0 |
| Silicone polymer of formula (Ib) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Alkalizing agent[4] | 0.05-15 | 0.5-10 | 1.5-8.0 | 3.5-7.5 |
| Cosmetic carrier[1] | Ad 100 | Ad 100 | Ad 100 | Ad 100 |

|  | AF 73 | AF 74 | AF 75 | AF 76 |
|---|---|---|---|---|
| Chromophoric compound[2] | 0.001-10 | 0.01-8.0 | 0.1-5.0 | 0.5-3.0 |
| Silicone polymer of formulas (Ia) and (Ib) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Alkalizing agent[4] | 0.05-15 | 0.5-10 | 1.5-8.0 | 3.5-7.5 |
| Cosmetic carrier[1] | Ad 100 | Ad 100 | Ad 100 | Ad 100 |

|  | AF 77 | AF 78 | AF 79 | AF 80 |
|---|---|---|---|---|
| Chromophoric compound | 0.001-10 | 0.01-8.0 | 0.1-5.0 | 0.5-3.0 |
| Silicone polymer of formula (Ia) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Alkalizing agent[4] | 0.05-15 | 0.5-10 | 1.5-8.0 | 3.5-7.5 |
| Thickener[5] | 0.0005-5.0 | 0.001-3.0 | 0.005-1.0 | 0.01-0.1 |
| Linear $C_8$-$C_{20}$ alcohol[6] | 5.0 to 25 | 8.0 to 20 | 10 to 18 | 12 to 16 |
| Cosmetic carrier[1] | Ad 100 | Ad 100 | Ad 100 | Ad 100 |

|  | AF 81 | AF 82 | AF 83 | AF 84 |
|---|---|---|---|---|
| Chromophoric compound[2] | 0.001-10 | 0.01-8.0 | 0.1-5.0 | 0.5-3.0 |
| Silicone polymer of formula (Ia) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Alkalizing agent[4] | 0.05-15 | 0.5-10 | 1.5-8.0 | 3.5-7.5 |
| Thickener[5] | 0.0005-5.0 | 0.001-3.0 | 0.005-1.0 | 0.01-0.1 |
| Linear $C_8$-$C_{20}$ alcohol[6] | 5.0 to 25 | 8.0 to 20 | 10 to 18 | 12 to 16 |
| Cosmetic carrier[1] | Ad 100 | Ad 100 | Ad 100 | Ad 100 |

|  | AF 85 | AF 86 | AF 87 | AF 88 |
|---|---|---|---|---|
| Chromophoric compound | 0.001-10 | 0.01-8.0 | 0.1-5.0 | 0.5-3.0 |
| Silicone polymer of formula (Ib) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Alkalizing agent[4] | 0.05-15 | 0.5-10 | 1.5-8.0 | 3.5-7.5 |
| Thickener[5] | 0.0005-5.0 | 0.001-3.0 | 0.005-1.0 | 0.01-0.1 |
| Linear $C_8$-$C_{20}$ alcohol[6] | 5.0 to 25 | 8.0 to 20 | 10 to 18 | 12 to 16 |
| Cosmetic carrier[1] | Ad 100 | Ad 100 | Ad 100 | Ad 100 |

|  | AF 89 | AF 90 | AF 91 | AF 92 |
|---|---|---|---|---|
| Chromophoric compound[2] | 0.001-10 | 0.01-8.0 | 0.1-5.0 | 0.5-3.0 |
| Silicone polymer of formula (Ib) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |
| Alkalizing agent[4] | 0.05-15 | 0.5-10 | 1.5-8.0 | 3.5-7.5 |
| Thickener[5] | 0.0005-5.0 | 0.001-3.0 | 0.005-1.0 | 0.01-0.1 |
| Linear $C_8$-$C_{20}$ alcohol[6] | 5.0 to 25 | 8.0 to 20 | 10 to 18 | 12 to 16 |
| Cosmetic carrier[1] | Ad 100 | Ad 100 | Ad 100 | Ad 100 |

|  | AF 93 | AF 94 | AF 95 | AF 96 |
|---|---|---|---|---|
| Chromophoric compound[2] | 0.001-10 | 0.01-8.0 | 0.1-5.0 | 0.5-3.0 |
| Silicone polymer of formulas (Ia) and (Ib) | 0.001-5.0 | 0.05-4.0 | 0.5-3.0 | 1.0-2.0 |
| Polyoxyethylen(10)-tridecylether | 0.003-1.5 | 0.006-1.1 | 0.009-0.8 | 0.015-0.3 |

-continued

| | | | | |
|---|---|---|---|---|
| Alkalizing agent[4] | 0.05-15 | 0.5-10 | 1.5-8.0 | 3.5-7.5 |
| Thickener[5] | 0.0005-5.0 | 0.001-3.0 | 0.005-1.0 | 0.01-0.1 |
| Linear $C_8$-$C_{20}$ alcohol[6] | 5.0 to 25 | 8.0 to 20 | 10 to 18 | 12 to 16 |
| Cosmetic carrier[1] | Ad 100 | Ad 100 | Ad 100 | Ad 100 |

[1] hydrous cosmetic carrier
[2] chromophoric compound selected from a mixture of oxidative dye precursors of the developer and coupler types and/or partially-oxidizing dyes,
[3] in formula (I), $R^1$ denotes methyl, B denotes NH, x denotes the integer 3, y denotes the integer 2 and t denotes the integer 1 or 2,
[4] mixture from monoethanolamine and 2-amino-2-methylpropan-1-ol
[5] thickening agent is selected from xanthangum, as well as the salts thereof, more particularly the sodium salts thereof,
[6] linear $C_8$-$C_{20}$ alcohol is selected from 2-octyldodecanol, cetearyl alcohol, as well as the mixtures thereof Embodiments AF 57 to AF 96 have a pH value from about 9.5 to about 11. It can also be envisaged that embodiments AF 1 to AF 94 contain an oxidant in the form of hydrogen peroxide in a quantity of from about 1 to about 7.5 wt. %, for example from about 1.25 to about 7 wt. %, such as from about 1.5 to about 6.0 wt. %, relative to the total weight of the embodiment concerned. The calculation of the total quantity refers to 100% $H_2O_2$.

For dyeing keratinous fibers, embodiments 1 to 94 of the cosmetic agents as contemplated herein described above achieve, due to the use of at least one hydroxy-terminated, aminized silicone polymers of formula (I) and/or (Ia) and/or (Ib), an excellent nourishing effect, more particularly combability, while avoiding a visible color shift, i.e. an ΔE-value of less than about 2, more particularly of less than about 1.

Oxidative dye compositions can also be produced immediately prior to application from two or more separately packaged compositions. This is useful for separating incompatible ingredients in order to prevent or inhibit a premature reaction. A separation into multi component systems is possible wherever the ingredients are expected to be or suspected of being incompatible. In such cases, the oxidative dye composition is produced by the consumer by mixing immediately prior to application. According to the present disclosure, this procedure with oxidative dyes, wherein the cosmetic agent as contemplated herein is first separated from an oxidant preparation, containing at least one oxidant, is exemplary.

Therefore, a further subject of the present disclosure is a kit-of-parts, comprising—separately packaged—
a) at least one container (C1), containing a cosmetic agent (M1) as contemplated herein, and
b) at least one container (C2), containing an oxidant agent preparation (M2), which contains in turn a cosmetically tolerated carrier at least one oxidant and at least one acid. The use of the at least one hydroxy-terminated, amine-functionalized silicone polymer in combination with specific quantities of oxidants unexpectedly results, when using the aforementioned kit-of-parts to produce cosmetic agents for dyeing keratinous fibers, in increased nourishment, more particularly to increased combability without, however, the addition of the non-ionic silicone polymer causing a color shift of ΔE> about 2, more particularly of ΔE> about 1, which is visible to the human eye.

According to the present disclosure, the term "container" is an envelope, which is present in the form of a possibly re-closable bottle, tube, jar, bag, sachet or similar envelopes. As contemplated herein, there are no restrictions with respect to the envelope material. However, envelopes from glass or plastic are identified as suitable for some embodiments.

The oxidants according to the present disclosure are different from atmospheric oxygen. Hydrogen peroxide, as well as the solid sediments for organic and inorganic compounds thereof, can be used as oxidants. As contemplated herein, the sediments for urea, melamine, polyvinyl-pyrrolidinon, as well as sodium borate, can be used as solid sediments. Hydrogen peroxide and/or one of the solid sediments for organic or inorganic compounds thereof are suitable oxidants. As contemplated herein, the oxidant is therefore selected from the group of persulphates, chlorites, hydrogen peroxide and adducts of hydrogen peroxide for urea, melamine, as well as sodium borate, for example hydrogen peroxide.

One embodiment of the present disclosure is therefore exemplified in that, as an oxidant, hydrogen peroxide is contained in a total quantity of from about 0.5 to about 15 wt. %, for example from about 0.75 to about 10 wt. %, such as from about 1 to about 7.5 wt. %, and in one embodiment from about 1.25 to about 7 wt. %, and in another embodiment from about 1.5 to about 6.0 wt. %, relative to the total weight of the oxidant preparation (M2). The calculation of the total quantity refers to 100% $H_2O_2$.

The oxidant preparations (M2) can also contain water in a total quantity of from about 40 to about 98 wt. %, for example from about 65 to about 85 wt. %, relative to the total weight of the oxidant preparation (M2).

According to one embodiment of the present disclosure, the oxidant preparations (M2) also contain at least one linear saturated alkanol with from about 12 to about 30 carbon atoms, for example with from about 16 to about 22 carbon atoms, in a total quantity of from about 0.1 to about 10 wt. %, for example from about 0.5 to about 5.0 wt. %, such as from about 1.0 to about 4.0 wt. %, relative to the total weight of the oxidant preparation (M2). Suitable examples include cetyl alcohol, stearyl alcohol, arachidyl alcohol, behenyl alcohol and lanolin alcohol or mixtures of said alcohols, as available for the large-scale hydration of plant and animal fatty acids. The mixture cetearyl alcohol is employed in one embodiment.

In another embodiment of the present disclosure, the oxidant preparations contain at least one ethoxylated non-ionic tenside, for example selected from tensides with the INCI designation ceteth-12, steareth-12, ceteareth-12, ceteth-20, steareth-20, ceteareth-20, ceteth-30, steareth-30, ceteareth-30, oleth-30, ceteareth-50, PEG-40 hydrogenated castor oil and PEG-60 hydrogenated castor oil, as well as mixtures of said substances, for example selected from ceteth-20, steareth-20, ceteareth-20, ceteth-30, steareth-30 and ceteareth-30, in a total quantity of from about 0.1 to about 10 wt. %, for example from about 0.5 to about 5.0 wt. %, such as from about 1 to about 4.0 wt. %, relative to the total weight of the oxidant preparation (M2).

According to the present disclosure, the oxidant preparations (M2) can also contain at least one ester from carboxylic acid with from about 10 to about 20 carbon atoms and one linear or branched alcohol with from about 1 to about 5 carbon atoms, for example isopropylmyristate, in a total quantity of from about 3.0 to about 25 wt. %, for example from about 5.0 to about 20 wt. %, such as from about 8.0 to about 15 wt. %, relative to the total weight of the oxidant preparation (M2).

According to an embodiment of the present disclosure, the oxidant preparations (M2) contain—relative to the total weight of the oxidant preparations (M2)—
- at least one linear saturated alcanol with from about 12 to about 30 carbon atoms in a total quantity of from about 0.1 to about 10 wt. %, for example from about 0.5 to about 5.0 wt. %, such as from about 1.0 to about 4.0 wt. %, further
- at least one ethoxylated non-ionic tenside, preferably selected from tensides with the INCI designation ceteth-12, steareth-12, ceteareth-12, ceteth-20, steareth-20, ceteareth-20, ceteth-30, steareth-30, ceteareth-30, oleth-30, ceteareth-50, PEG-40 hydrogenated castor oil and PEG-60 hydrogenated castor oil, as well as mixtures of said substances, for example selected from ceteth-20, steareth-20, ceteareth-20, ceteth-30, steareth-30 and ceteareth-30, in a total quantity of from about 0.1 to about 10 wt. %, for example from about 0.5 to about 5.0 wt. %, such as from about 1.0 to about 4.0 wt. %, as well as
- at least one ester from a carboxylic acid with 10 to 20 carbon atoms and one linear or branched alcohol with from 1 to about 5 carbon atoms, preferably isopropylmyristate, in a total quantity of from about 3.0 to about 25 wt. %, for example from about 5.0 to about 20 wt. %, such as from about 8.0 to about 15 wt. %.

The oxidant preparations (M2) as contemplated herein also contain at least one acid. Exemplary acids are selected from dipicolinic acids, food acids, such as citric acid, acetic acid, malic acid, lactic acid and tartaric acid, diluted mineral acids such as hydrochloric acid, phosphoric acid, pyrophosphoric acid and sulphuric acid, as well as mixtures thereof. These acids are suitable for setting an acid pH value of the oxidant preparation (M2). It is therefore desirable for the oxidant preparations (M2) to have a pH value in the range of from about 2 to about 5, more particularly from about 3 to about 4.

To produce oxidative dye compositions from the kit-of-parts as contemplated herein, the cosmetic agent (M1) as contemplated herein is mixed in the container (C1) with the oxidant preparation (M2) in container (C2) or vice versa. In this context, it is desirable as contemplated herein for the mixture ratio of the cosmetic agent (M1) to the oxidant preparation (M2) to be from about 4:1 to about 1:4, for example from about 3:1 to about 1:3, such as from about 2:1 to about 1:2.

It can also be advantageous as contemplated herein for the kit-of-parts to have a further hair treatment agent, for example a conditioner preparation, in an additional container. This conditioner preparation contains, advantageously, at least one conditioning agent, selected from the group of cationic polymers, silicone derivatives and oils. Moreover, the kit-of-parts can comprise application aids, such as combs, brushes, applicators or brushes, personal protective clothing, for example disposable gloves, as well as instructions for use. An applicator is a wide brush, located at the stem end of which is a tip, which permits and simplifies the division of fiber bundles and/or hair strands from the total quantity of fibers.

With respect to the cosmetic agent (M1) as contemplated herein in container (C1) and the oxidant preparation (M2) in container (C2), the statements made about the cosmetic agents as contemplated herein apply mutatis mutandis.

A further subject matter of the present disclosure is a method for dyeing keratinous fibers with increased nourishment while minimizing the color shift at the same time, the method including the following method steps, which is some embodiments may optionally be performed in the sequence indicated:
a) Provision of a cosmetic agent as contemplated herein (M1),
b) Provision of an oxidant preparation (M2), containing in a cosmetically tolerated carrier at least one oxidant and at least one acid,
c) Mixing of the cosmetic agent (M1) with the oxidant preparation (M2),
d) Application of the mixture obtained in Step c) onto the keratinous fibers and leaving said mixture on the keratinous fibers for a period of from about 10 to about 60 minutes, for example from about 20 to about 45 minutes, at room temperature and/or at least about 15° C., such as at least about 30° C.
e) rinsing the keratin fibers with water and/or a cleansing composition for from about 1 to about 5 minutes, and
f) possibly applying a post-treatment agent to the keratin fibers and rinsing off after a period of from about 1 to about 10 minutes.

The method as contemplated herein for dyeing keratinous fibers using a special hydroxy-terminated, amine-functionalized silicone polymer results in an improved nourishment of the dyed keratinous fibers, without the addition of the special hydroxy-terminated, amine-functionalized silicone polymer leading to an unwanted color shift of $\Delta E >$ about 2, for example of $\Delta E >$ about 1, which is visible to the human eye.

Room temperature according to the present disclosure means the ambient temperature that prevails without the effect of external heat and amounts to preferably from about 10 to about 39 degrees C. The effect of the coloring or lightening preparation can be increased through an external heat supply, by employing a heating hood for example. preferred suitable exposure time of the coloring and/or lightening preparation on the keratinous fibers is from about 10 to about 60 min, for example from about 20 to about 45 min. At the end of the exposure period, the remaining dye is washed out of the keratinous fibers by employing a cleansing preparation, which may contain at least one cationic and/or anionic and/or non-ionic tenside. The process is repeated with further cleansing preparations as necessary. After the washing out step, the keratinous fibers are rinsed, as necessary, with a post-treatment agent, a conditioning agent for example, and then dried with a hand towel or a hot air blower. The dye preparation is normally applied by hand by the user. Personal protective clothing is preferably worn in the process, more particularly protective gloves, made of a synthetic material or latex for one-time use (disposable gloves), as well as an apron where applicable. However, the dyes can also be applied to the keratin fibers by employing an application aid.

As contemplated herein, each of method steps a) to f) are preferably carried out with a time interval between the individual process steps of from about 0 to about 40 minutes, for example from 0 to 30 minutes.

With respect to the cosmetic agent (M1), the oxidant preparation (M2) and other exemplary embodiments of the method as contemplated herein, the statements made about the cosmetic means and the kit-of-parts as contemplated herein apply mutatis mutandis.

Moreover, a further subject matter of the present disclosure is the use of a cosmetic agent as contemplated herein for increasing the nourishment of keratinous fibers while minimizing the color shift at the same time. The use of cosmetic agents having a special, hydroxy-terminated, amine-functionalized silicone polymer results in an increased nourishing of the dyed keratinous fibers, without the addition of said nourishing agent causing an unwanted color shift of $\Delta E>$ about 2, for example of $\Delta E>$ about 1, which is visible to the human eye.

With respect to the exemplary embodiments of the use as contemplated herein, the statements made about the cosmetic agent as contemplated herein and to the kit-of-parts as contemplated herein apply mutatis mutandis.

Finally, a further subject matter of the present disclosure is the use of a kit-of-parts as contemplated herein for producing a cosmetic agent for coloring keratinous fibers with increased nourishing while minimizing the color shift at the same time. The use of a nourishing agent in the form of a special, hydroxy-terminated, amine-functionalized silicone polymer in the kit-of-parts results, with the production of dyes, in an increased nourishing of the dyed keratinous fibers, without the addition of said nourishing agent causing an unwanted color shift of $\Delta>$ about 2, for example of $\Delta E>$ about 1, which is visible to the human eye.

With respect to the preferred embodiments of the use as contemplated herein, the statements made about the cosmetic agent as contemplated herein and to the kit-of-parts as contemplated herein apply mutatis mutandis.

The examples below are intended to explain the exemplary embodiments of the present disclosure without having any limiting effect.

EXAMPLES

1. Recipes

Compositions of the used cosmetic agents (oil-in-water emulsions, all quantities in wt. %). The hydroxy-terminated, amine-functionalized silicone polymer used in the formulations below is for example a silicone polymer of formulas (Ia) and/or (Ib).

| Raw material | V1 | E1* | E2* |
|---|---|---|---|
| Xanthan Gum | 0.1 | 0.1 | 0.1 |
| 2-octyldodecanol | 2.3 | 2.3 | 2.3 |
| Lanette N[a)] | 14 | 14 | 14 |
| Cetearyl alcohol | 3.9 | 3.9 | 3.9 |
| Glycerine monostearate | 6.0 | 6.0 | 6.0 |
| Glycerol 99.5% | 2.0 | 2.0 | 2.0 |
| Coconut amidopropylbetaine, 40% | 2.0 | 2.0 | 2.0 |
| Monoethanolamine | 4.4 | 4.4 | 4.4 |
| 2-Amino-2-methylpropanol | 0.10 | 0.10 | 0.10 |
| Sodium sulfite, anhydrous | 0.30 | 0.30 | 0.30 |
| Caramel syrup, 75% | 0.10 | 0.10 | 0.10 |
| Grape seed oil | 1.0 | 1.0 | 1.0 |
| 1-hydroxyethyl-4,5-diamino pyrazole sulfate | 1.5 | 1.5 | 1.5 |
| 4-amino-3-methylphenol | 0.10 | 0.10 | 0.10 |
| p-Amino-o-cresol | 0.20 | 0.20 | 0.20 |
| m-aminophenol | 0.60 | 0.60 | 0.60 |
| Non-ionic silicone polymer** | — | 0.70 | 1.4 |
| Water, fully-demineralized | ad 100 | ad 100 | ad 100 |

*as contemplated herein
**Active substance
[a)]INCI designation: Cetearyl alcohol, Sodium cetearyl sulfate (BASF)

The fat basis was fused together at 80° C. and dispersed with a portion of the water quantity. The remaining recipe constituents were then gradually incorporated by agitation. Water was then added to 100 wt. % and the formulation was agitated cold. Formula V1 is a formula similar to that of the present disclosure without hydroxy-terminated, amine-functionalized silicone polymers. Formulas E1 and E2 are examples as contemplated herein.

Oxidant preparation O1 (all quantities in wt. %)

| Raw material | O1 |
|---|---|
| Di-sodium pyrophosphate | 0.10 |
| Dipicolinic acid | 0.10 |
| Potassium hydroxide 50% | 0.30 |
| 1-Hydroxyethan-1,1-diphosphonic acid 60% | 40 |
| Fatty alcohol sulfate $C_{16}$-$C_{18}$ sodium salt | 0.30 |
| Eumulgin RO 40[b)] | 0.60 |
| Cetearyl Alcohol | 3.6 |
| Ceteareth-20 | 0.50 |
| Beeswax | 0.30 |
| Isopropyl myristate | 10 |
| Hydrogen peroxide 50% | 11 |
| Water, fully-demineralized | ad 100 |

[b)]INCI designation: PEG-40 Castor oil (BASF)

2. Minimal Color Shift Caused by the Addition of the Hydroxy-terminated, Amine-functionalized Silicone Polymer To produce the oxidative dye for determining the color shift, the cosmetic agents V1, as well as E1 and E2, were mixed with the aforementioned oxidant preparation O1 in a total ratio of 1:1.

The oxidative dyes thus produced were each applied in defined amounts (4 g of oxidative dye per 1 g of yak hair) on yak hair (12 strands per oxidative dye) and left on the hair strands for an exposure period of 30 minutes at 32° C. The remaining agents were then rinsed out of the hair strands with lukewarm water for 2 minutes each, the strands first being dried with a hand towel and then blown dry.

All strands were measured with a colorimeter from Datacolor, type Spectraflash 450. The values $\Delta E$ used to assess the color shift are derived from the L*a*b color measurements taken on the respective strands:

$$\Delta E=((L_i-L_0)^2+(a_i-a_0)^2+(b_i-b_0)^2)^{1/2}$$

$a_0$, $b_0$ and $L_0$ are the mean values of the color measurements on the yak strands colored using V1, determined from 12 measurements. $a_i$, $b_i$ and $L_i$ denote the mean values of the color measurements, which are obtained for yak hair strands colored using E1 and/or E2.

The greater the value for $\Delta E$, the more pronounced the color difference or "color shift". Color differences with an $\Delta E<1$ are not perceptible to the human eye. Color differences with an $\Delta E<2$ are visible to the trained eye. Color differences with an $\Delta E>2$ are visible even to the untrained eye. The table below shows the $\Delta E$ values for the coloration using cosmetic agents E1 and E2 in comparison to V1. The colorations using cosmetic agents E1 and E2 as contemplated herein, which contain at least one special, hydroxy-terminated, amine-functionalized silicone in a total quantity of 0.70 wt. % and/or 1.4 wt. %, have only a minimal color shift of $\Delta E<2$, which is not visible to the untrained eye. The higher the quantity of the hydroxy-terminated, amine-functionalized silicone polymer used, the lower the color shift caused by the special silicone polymer.

| Oxidative dye | ΔE |
|---|---|
| E1 + O1 (1:1) | 1.49 |
| E2 + O1 (1:1) | 0.58 |

3. Improved Nourishment

To produce the oxidative dye for determining the nourishment, the cosmetic agents V1, E1 and E2 were each mixed with the aforementioned oxidant preparation O1 in a total ratio of 1:1.

12 strands of naturally light-brown European hair (IHIP (New York), lot #03/2012, N104, length 15 cm, weight 1 g) were washed in an aqueous sodium lauryl ether sulfate solution (3% active substance content in the solution). The strands were dried in the atmosphere and stored for 24 hours at 25° C. and 25% relative air humidity. Once these stands had soaked in water for 5 minutes, their wet combability was determined (reference value).

For the colorations, 12 strands of naturally European hair (IHIP (New York), lot #03/2012, N104, length 15 cm, weight 1 g) were used with each oxidative dye. 4 g of the produced oxidative dye were applied to every 1 g of hair strands. Once the strands had been dyed for 30 min at 32° C., they were rinsed in water for 2 min and dried in the atmosphere.

The wet combability measurement was taken as follows:

Before the measurement, each strand was moistened with water while being combed with a hard, fine-toothed rubber comb (from Hercules Sägemann, Hamburg Germany) for 2 seconds. At the end of 3 combing operations was carried out, the combing strength was measured over a further 10 combing operations, the respective hair strands being slowly rotated during the combing operation. The measurements obtained are compared using the following statistical tests embedded in the Statistica 10.0 software (StatSoft Inc., USA):

Shapiro-Wilks Test (test for normal distribution)
Outlier test according to Grubbs
Bartlett Test (test for homoscedasticity of variances)
Uni-variant significance test
Newman-Keuls Test (determination of significant differences)
Unequal N HSD Test (test for multiple comparisons).

The change in combing force dK in percent can be calculated using formula $dK=[(K_0-K_i)/K_0]*100$. $K_0$ is the mean value of the combing force for the un-dyed hair strands and $K_i$ is the mean value of the hair strands treated with the oxidative dye.

The lower the combing force applied, and hence the greater the change in the combing force, the greater the nourishment of the hair strands. The table below shows the dK values for the coloration using cosmetic agents V1, E1 and E2. Coloration using cosmetic agents E1 and E2 as contemplated herein, which contain at least one special hydroxy-terminated, amine-functionalized silicone polymer in a total quantity of 0.70 and/or 1.4 wt. %, leads to a higher change in the combing force and hence increased nourishment compared to coloration without hydroxy-terminated, amino-functionalized silicone polymers (V1).

| Oxidative dye | dK [%] |
|---|---|
| V1 + O1 (1:1) | 1 |
| E1 + O1 (1:1) | 17 |
| E2 + O1 (1:1) | 24 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Cosmetic agent for coloring keratin fibers, comprising in a cosmetically tolerant carrier
   a) at least one chromophoric compound, selected from the group of oxidative dye precursors, partially-oxidative dyes and the mixtures thereof,
   b) at least one hydroxy-terminated amine-functionalized silicone polymer of formula (I)

$$(O_{1/2}H)_t[A]_a \quad (I)$$

where $A=(SiO_{4/2})_k(R^1SiO_{3/2})_m(R^1{}_2SiO_{2/2})_p$
$(R^1{}_3SiO_{1/2})_q(O_{2/2}SiR^1\text{---}(CH_2)_x\text{---}B\text{---}(CH_2)_y\text{---}$
$NH_2)_s(O_{1/2}SiR^1R^2\text{---}(CH_2)_x\text{---}B\text{---}(CH_2)_y\text{---}$
$NH_2)_r$, wherein the at least one hydroxy-terminated amine-functionalized silicone polymer of formula (I) is terminated at a first end with a hydroxy group and is terminated at a second end with an amine group, a denotes integers from 1 to 20,000, wherein, if a ≥2, the respective values k, m, p, q, s and r in a structural element A can be selected irrespective of previous structural elements A, $R^1$ and $R^2$ denote, independently of one another, hydrogen, a OH group, a linear or branched $C_1$-$C_{12}$-alkyl group, a phenyl group or a vinyl group, B denotes an oxygen atom, a NH group or sulfur, x and y denote, independently of one another, integers from 1 to about 10, t denotes integers from 1 to 5, and the total of k+m+p+q+s+r denotes integers from 3 to about 20,000.

2. Cosmetic agent according to claim 1, wherein formula (I) for radical $R^1$ denotes a methyl group and B denotes a NH group.

3. Cosmetic agent according to claim 1, wherein formula (I) x denotes the integer 3, y denotes the integer 2 and t denotes integers 1 or 2.

4. Cosmetic agent according to claim 1, wherein a hydroxy-terminated, amine-functionalized silicone polymer of formula (Ia) represents the hydroxy-terminated, amine-functionalized silicone polymer of formula (I)

$$(O_{1/2}H)_t[A]_a \quad (Ia)$$

where $A=(R^1{}_2SiO_{2/2})_p(O_{2/2}SiR^1\text{---}(CH_2)_x\text{---}B\text{---}$
$(CH_2)_y\text{---}NH_2)_s$ wherein a denotes integers from 1 to about 1,000, wherein, if a ≥2, the respective values p and s in a structural element A can be selected irrespective of previous structural elements A, $R^1$ denotes a methyl group, B denotes a NH group, x denotes the integer 3, y denotes the integer 2,
t denotes integers 1 or 2,
p denotes integers from about 8 to about 1,000, and
s denotes integers from 1 to about 800.

5. Cosmetic agent according to claim 1, wherein a hydroxy-terminated, amine-functionalized silicone polymer of formula (Ib) represents the hydroxy-terminated, amine-functionalized silicone polymer of formula (I)

  (Ib)

where 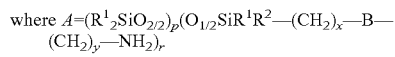

wherein
a denotes integers from 1 to about 1,000, wherein, if a ≥2, the respective values p and r in a structural element A can be selected irrespective of previous structural elements A,
$R^1$ and $R^2$ each denote a methyl group, B denotes a NH group,
x denotes the integer 3, y denotes the integer 2,
t denotes integers 1 or 2,
p denotes integers from about 8 to about 1,000, and r denotes integers from 1 to about 800.

6. Cosmetic agent according to claim 1, wherein the cosmetic agent comprises the at least one hydroxy-terminated, amine-functionalized silicone polymer b) in a total quantity of from about 0.001 to about 5.0 wt. %, relative to the total weight of the cosmetic agent.

7. Cosmetic agent according to claim 1, wherein the cosmetic agent comprises in addition polyoxyethylene(10)-tridecylether in a total quantity of from about 0.003 to about 1.5 wt. %, relative to the total weight of the cosmetic agent.

8. Cosmetic agent according to claim 1, wherein said cosmetic agent comprises in addition at least one further compound, selected from the group of (i) thickening agents; (ii) linear or branched, saturated or unsaturated alcohols having about 8 to about 20 carbon atoms; (iii) tensides; (iv) alkalizing agents; (v) oils; or (vi) mixtures thereof.

9. Cosmetic agent according to claim 8 wherein the thickening agents include at least one naturally occurring thickening agent in a total quantity of from about 0.0005 to about 5.0 wt. %, relative to the total weight of the cosmetic agent.

10. Cosmetic agent according to claim 8, wherein at least one amphoteric tenside, selected from amidopropylbetaines having from about 9 to about 13 carbon atoms in the acyl group, is included, as the tenside, in a total quantity of from about 0.1 to about 5.0 wt. %, relative to the total weight of the cosmetic agent.

11. Cosmetic agent according to claim 8, wherein a mixture of at least two different alkanolamines are included, as the alkalizing agent, in a total quantity of from about 0.05 to about 15 wt. %, relative to the total weight of the cosmetic agent.

12. Package unit (kit-of-parts), comprising—separately packaged—
a) at least one container (C1), comprising a cosmetic agent (M1) according to claim 1, and
b) at least one container (C2), comprising an oxidant agent preparation (M2), which comprises in turn a cosmetically tolerated carrier at least one oxidant and at least one acid.

13. Method for dyeing keratinous fibers with increased nourishment while minimizing the color shift at the same time, the method comprising the following method steps in the sequence indicated:
a) Provision of a cosmetic agent (M1) according to claim 1,
b) Provision of an oxidant preparation (M2), comprising in a cosmetically tolerated carrier at least one oxidant and at least one acid,
c) Mixing of the cosmetic agent (M1) with the oxidant preparation (M2),
d) Application of the mixture obtained in Step c) onto the keratinous fibers and leaving said mixture on the keratinous fibers for a period of from about 10 to about 60 minutes at room temperature or at least about 15° C.,
e) Rinsing the keratin fibers with water and/or a cleansing composition for from about 1 to about 5 minutes, and
f) where applicable applying a post-treatment agent to the keratin fibers and rinsing off after a period of from about 1 to about 10 minutes.

14. Cosmetic agent according to claim 1, wherein the cosmetic agent comprises the at least one hydroxy-terminated, amine-functionalized silicone polymer b) in a total quantity of from about 0.05 to about 4.0 wt. %, relative to the total weight of the cosmetic agent.

15. Cosmetic agent according to claim 1, wherein the cosmetic agent comprises in addition polyoxyethylene(10)-tridecylether in a total quantity from about 0.006 to about 1.1 wt. %, relative to the total weight of the cosmetic agent.

16. Cosmetic agent according to claim 8, wherein the thickening agents include xanthan gum in a total quantity of from about 0.001 to about 1.0 wt. %, relative to the total weight of the cosmetic agent.

17. Cosmetic agent according to claim 8, wherein at least one amphoteric tenside, selected from amidopropylbetaines having from about 9 to about 13 carbon atoms in the acyl group, is included, as the tenside, in a total quantity of from about 0.2 to about 2.0 wt. %, relative to the total weight of the cosmetic agent.

18. Cosmetic agent according to claim 8, wherein the alkalizing agents include monoethanolamine and 2-amino-2-methylpropan-1-ol in a total quantity of from about 0.5 to about 10 wt. %, relative to the total weight of the cosmetic agent.

* * * * *